United States Patent [19]

Gooden

[11] 4,109,652
[45] Aug. 29, 1978

[54] METHOD FOR REGULATING CHARACTERISTICS OF A GAS STREAM

[76] Inventor: Alan L. Gooden, 1214 5th Ave., Neptune, N.J. 07753

[21] Appl. No.: 679,340

[22] Filed: Apr. 22, 1976

[51] Int. Cl.$^2$ ............................................. A61M 15/00
[52] U.S. Cl. .................................... 128/212; 128/192; 261/DIG. 65; 165/509
[58] Field of Search ............... 128/192, 193, 194, 186, 128/212, 367, 400, 204, 402, 191 A, 1 B, 375, 399, 368, 256; 261/151, 83, 84, 92, DIG. 65, DIG. 15; 165/59, 60

[56] References Cited

U.S. PATENT DOCUMENTS

| 2,302,023 | 11/1942 | Glasser | 128/204 |
|---|---|---|---|
| 3,229,450 | 1/1966 | Stern | 128/186 |
| 3,240,262 | 3/1966 | Nybolet | 165/60 |
| 3,255,751 | 6/1966 | Bouet | 128/367 |
| 3,345,047 | 10/1967 | Gooden | 265/DIG. 15 |
| 3,526,226 | 9/1970 | Stern | 128/192 |
| 3,565,072 | 2/1972 | Gauthier | 128/212 |
| 3,902,488 | 9/1975 | Sheppard | 128/367 |

FOREIGN PATENT DOCUMENTS 821,003  9/1959  United Kingdom ..................... 261/151

*Primary Examiner*—Robert W. Michell
*Assistant Examiner*—Henry J. Recla
*Attorney, Agent, or Firm*—Roger A. Clapp

[57] ABSTRACT

A method for regulating temperature and other characteristics of a gas stream flowing in a system is disclosed wherein a liquid is divided into droplets, the droplets are introduced directly into the gas stream to establish a heat exchange interface and the temperature of the liquid is regulated in order to maintain the temperature of the gas stream at a predetermined level at a predetermined target location in the system.

9 Claims, No Drawings

METHOD FOR REGULATING CHARACTERISTICS OF A GAS STREAM

BACKGROUND OF THE INVENTION

1. Field of the Invention

This invention relates to techniques for using a gas stream to conrol an environment and pertains in particular to methods for controlling temperature and other characteristics of the gas stream.

2. Description of the Prior Art

Temperature control of a gas stream is typically achieved through an interface where the gas stream and the heat source or sink interact. Heretofore, however, the interface has been of limited application. For example, in the conventional hot air furnace system, the interface is a metal plenum which readily exchanges heat, but is incapable of other functions. That is, it does not readily lend itself to chemical or other simultaneous treatment of the gas stream.

Accordingly, one object of this invention is to achieve gas stream heat exchange in a way which is simple yet capable of simultaneously performing other functions.

Gas streams are used in a wide variety of ways to control environment, but a particularly important application is in the treatment of medical patients. When it is necessary to control the respiration of a medical patient as, for example, during a surgical procedure in which anesthesia is being administered, the patient should breathe in a controlled environment. If the environment in which the patient breathes is part of a conducted system, the atmosphere becomes a gas stream which can be treated to control the constituents thereof such as oxygen, carbon dioxide, nitrous oxide, other anesthetic vapors and the like.

While breathing systems are available in which the constituency of the gas stream is controllable, such systems are not readily amenable to control of the gas stream temperature. Consequently, the gas stream often reaches the patient at much less than body temperature thereby necessitating the application to the patient of external heat in order to avoid dangerous drops in body temperature.

Accordingly, another object of this invention is to maintain the temperature of a gas stream reaching a patient's respiratory tract within a physiologically beneficial range.

Regulating the heat of a gas stream in such systems, however, is not a simple matter. Where the environment and the gases are temperature sensitive, for example, safety code limitations must not be exceeded. Moreover, once a patient has been placed in the system and system pressures are stabilized, pressure changes must be avoided which would adversely interfere with established breathing patterns. That is, any regulation of the gas stream may not interfere with the spontaneous or assisted respiration of the patient or with conventional techniques of administering anesthesia.

Accordingly, another object of this invention is to achieve safe, simple and efficient temperature control of the gas stream without disturbing established practices.

SUMMARY OF THE INVENTION

In accordance with the preferred embodiment of the invention, the temperature of a gas stream flowing in a system is flexibly regulated by disbursing particles of a heat absorbing medium into the gas stream so that heat is exchanged between the gas stream and the particles and then adjusting the temperature of the medium so as to control temperature of the gas stream; i.e., at a downstream trarget location.

In accordance with one feature of this invention, an efficient heat exchange between the gas stream and the particles is achieved without interference with other system parameters by using liquid as the heat absorbing medium and dividing the liquid into droplets small enough to expose a large surface area to the gas stream, but large enough to discourage entrainment of the droplets in the gas stream.

In accordance with another feature of this invention, the droplets are flicked or snapped from the liquid body so that their introduction into the gas stream does not interfere with other system parameters.

A better understanding of these and other features and objects of the invention will be facilitated by the following detailed description.

DETAILED DESCRIPTION OF THE INVENTION

In accordance with this invention, a heat absorbing medium divided into heat absorbing particles is disbursed through a gas stream which flows in a system so that the gas stream makes direct contact with the surface of the particles. Next, temperature of the medium is adjusted to create a gradient in which the temperature of the particles differs from the temperature of the gas stream so that a heat exchange occurs when the particles and gas stream interact. Thereafter, particle temperature is further adjusted until the rate of heat exchange between the particles and gas stream causes the gas stream to reach a desired temperature at a preselected location, for example, a downwstream target location in the system.

A particular advantage of this method is that exchanges other than heat can occur between the gas stream and the particles as they interface. For example, the particles could carry, or be composed of, a material suitable for combination with, or transfer to, the gas stream; i.e., the particles could carry or be droplets of a volatile liquid suitable for chemically treating the gas stream or elements through which the gas stream passes.

In a preferred embodiment of the invention, the gas stream flows in a conducted system designed to deliver a controlled atmosphere to a specific target area; i.e., the respiratory tract of a medical patient during a surgical procedure. In that application, the heat absorbing medium is advantageously a liquid, and the gas stream comprises a precise mixture of gases such as oxygen, anesthesia and the like which can be moved through the system by the patients own respiration. The heat exchange between the liquid and the gas is achieved by dividing the liquid into droplets and disbursing the droplets into the gas stream. Finally, the temperature of the gas stream at the patient's resiratory tract is monitored and the temperature of the liquid is controlled so that heat exchange occurs at a rate necessary to maintain the patient's respiratory tract at a desired level; for example, body temperature, with a few degrees of body temperature or, for that matter, anywhere within a range of 50° to 100° fahrenheit.

In practicing this embodiment of the invention, however, it is often important that the droplets be disbursed into the gas stream exclusively; that is, without an attendant carrier which might disturb or contaminate the mixture or composition of the gas stream. Moreover, it is extremely important that the dispersion of the droplets into the gas stream be accomplished without clogging and without interference with the pressure levels in the system. That is, the established pressure levels must not be changed, or the respiratory burden on the patient will be disturbed which, in turn, could lead to the need for a respirator. Likewise, such pressure changes would be reflected throughout the system and, as a consequence, could disturb vaporization rates taking place therein; i.e., between anesthetic vaporizers and oxygen.

In addition, it is extremely important that entrainment of the droplets in the gas stream be subject to regulation. For example, if too many droplets are entrained, the patient's alveoli and lung surface mucosa will quickly attract and retain moisture to dangerously high levels. On the other hand, occasions may arise where it is desirable that some of the droplets reach the patients lungs; i.e., where the liquid includes medicinally active ingredients. In general, however, the droplets must be small enough to expose a large surface area to the gas stream so as to obtain efficient heat exchange, but large enough so as to discourage ready transportation by the gas as it flows.

Finally, it is imperative that the temperatures experienced by the system not be excessive. Safety codes are strict in medical applications, so the temperatures necessary to establish the required gradients must be kept within allowable limits.

A particularly advantageous way of controlling droplet size and exclusively introducing the droplets into the gas stream without clogging and without pressure disturbance is to divide and disburse the liquid by a snapping or flicking action. The desired snapping action can readily be achieved by wetting an elongated spine or bristle and then setting the bristle in motion so that the mass of the liquid becomes great enough to break off a droplet. An example of creating a droplet in that manner would be to sequentially bring stiff bristles into contact with a wetting liquid. Thereafter, each bristle, after it leaves the liquid, is rapidly moved; i.e., spun or deflected and then suddenly released. When the bristle tip reaches an appropriate velocity, liquid running down the bristle will be flung or snapped off the end as, for example, when the bristle flicks back into the undeflected state. If the gas stream is passed over the flicking bristles, the droplets will be widely disbursed therein. Moreover, with this technique droplet size can readily be adjusted by controlling the speed at which the bristles move. Finally, by regulating temperature of the liquid, the desired heat exchange can be achieved at temperatures readily kept within safety code standards; i.e., at less than the liquid boiling point.

The foregoing discussion has tacitly assumed non-volatility of the liquid, but it may alternatively be volatile without unduly affecting the temperature regulating features of the disclosed method. If it is volatile, however, other advantages become available. For example, humidity of the gas stream can be controlled at the same time temperature is controlled. Moreover, the disclosed methods contemplate using the liquid for other functions. For example, the liquid can itself be a medicinal preparation or it can serve as a carrier for delivering medication to a patient or for treatment of the gas stream.

While the embodiment disclosed have primarily involved medicinal uses, it must be recognized that the principles of the invention permit much broader application. At bottom, the disclosed techniques provide a highly efficient heat exchanger which can be used to control the gas stream temperature; that is, it can readily cool up stream locations or heat or cool down stream locations. Consequently, the gas stream can serve as the operative part of other devices such as a combination furnance-central air conditioning system. Moreover, when the heat exchanging medium is water, the gas stream can be simultaneously humidified.

In summary, a method has been disclosed in which a gas stream flowing in a system is used to achieve temperature control of portions of the system without interference with other parameters therein. Moreover, the disclosed method achieves that result in a way which permits wide flexibility in obtaining other advantages. While only one embodiment of the invention has been disclosed, it is merely illustrative of the principles of the invention and many other embodiments falling within the scope of the invention will readily occur to those skilled in the art.

What I claim is:

1. In a process for regulating the characteristics of a gas stream flowing in a system serving a respiratory tract, the steps of:

temperature treating a liquid;

dividing said temperature treated liquid into liquid droplets independently of said gas stream;

introducing said liquid droplets into direct contact with said gas stream while maintaining said droplet introduction and gas stream flow separate and distinct from each other so that any change in one will be independent of the other and (passively with respect to the flow dynamics of the gas stream) so that heat can be exchanged between said gas stream and said droplets when they interface without affecting system pressure or flow;

conducting said gas stream to said respiratory tract after interfacing with said droplets; and regulating the temperature of said liquid so as to establish and maintain the temperature of said gas stream at a desired level at said respiratory tract.

2. The process steps in accordance with claim 1 wherein the temperature of said gas stream at said respiratory tract is maintained within the range of 50° to 100° fahrenheit.

3. The process steps in accordance with claim 2 wherein the temperature of said gas stream at said respiratory tract is maintained substantially at 94° fahrenheit.

4. The process steps in accordance with claim 1 further including the step of introducing additives into said liquid for interaction with said gas stream when interface occurs.

5. The process steps in accordance with claim 4 wherein said additives are medically active.

6. The process steps in accordance with claim 1 wherein said droplets are momentarily introduced into said gas stream.

7. The process steps in accordance with claim 1 wherein said droplets mechanically thrust into said gas stream.

8. The process steps in accordance with claim 1 wherein said liquid is divided into droplet small enough to expose a large surface area to said gas stream but large enough to discourage entrainment therein.

9. The process steps in accordance with claim 1 wherein said liquid is volatile.

* * * * *